US010665338B2

(12) United States Patent
Cohen et al.

(10) Patent No.: US 10,665,338 B2
(45) Date of Patent: May 26, 2020

(54) AUTOMATIC IDENTIFICATION OF MULTIPLE ACTIVATION PATHWAYS

(71) Applicant: BIOSENSE WEBSTER (ISRAEL) LTD., Yokneam (IL)

(72) Inventors: Benjamin Cohen, Haifa (IL); Aharon Turgeman, Zichron Ya'acov (IL); Lior Zar, Poria Illit (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/902,554

(22) Filed: Feb. 22, 2018

(65) Prior Publication Data

US 2019/0259490 A1 Aug. 22, 2019

(51) Int. Cl.
*G16H 30/20* (2018.01)
*A61B 5/00* (2006.01)
(Continued)

(52) U.S. Cl.
CPC ........... *G16H 30/20* (2018.01); *A61B 5/0402* (2013.01); *A61B 5/044* (2013.01); *A61B 5/04012* (2013.01); *A61B 5/0538* (2013.01)

(58) Field of Classification Search
CPC ................................. G16H 30/20; A61B 5/044
(Continued)

(56) References Cited

U.S. PATENT DOCUMENTS 5,999,288 A * 12/1999 Ellinas ................ H04J 14/0227
398/59
8,456,182 B2 6/2013 Bar-Tal et al.
(Continued)

FOREIGN PATENT DOCUMENTS

CN 106725448 A 5/2017
EP 3254618 A1 12/2017

OTHER PUBLICATIONS

Aurenhammer, Franz, "Voronoi Diagrams—A Survey of a Fundamental Geometric Data Structure", ACM Computing Surveys, Sep. 1991, pp. 345-405, vol. 23, No. 3.
(Continued)

*Primary Examiner* — Hai Tao Sun
(74) *Attorney, Agent, or Firm* — Dergosits & Noah LLP; Todd A. Noah

(57) ABSTRACT

Described embodiments include a method that includes constructing a computerized electroanatomical model of a portion of a heart, the model including a mesh, which approximates the portion of the heart, and a plurality of points, at different respective locations on the mesh, having respective associated local activation times (LATs) that were ascertained from electrocardiographic signals acquired from the portion. The method further includes constructing a graph that interconnects the points and, based on the respective locations and LATs of the points, identifying, from a plurality of pathways, through the graph, from a first one of the points having a lowest one of the LATs to a second one of the points having a highest one of the LATs, both a shortest pathway and a longest pathway. The method further includes displaying the mesh, with the identified shortest pathway and longest pathway superimposed over the mesh. Other embodiments are also described.

15 Claims, 3 Drawing Sheets

(51) Int. Cl.
*A61B 5/044* (2006.01)
*A61B 5/04* (2006.01)
*A61B 5/0402* (2006.01)
*A61B 5/053* (2006.01)

(58) Field of Classification Search
USPC .......................................................... 345/420
See application file for complete search history.

(56) References Cited

U.S. PATENT DOCUMENTS

| | | | |
|---|---|---|---|
| 2005/0093862 A1* | 5/2005 | Boier-Martin | G06T 17/20 345/420 |
| 2008/0137927 A1* | 6/2008 | Altmann | A61B 8/4488 382/131 |
| 2008/0225044 A1* | 9/2008 | Huang | G06T 17/00 345/420 |
| 2011/0207479 A1 | 8/2011 | Ioppe et al. | |
| 2013/0035244 A1 | 2/2013 | Albou | |
| 2013/0054603 A1 | 2/2013 | Birdwell et al. | |
| 2016/0183824 A1* | 6/2016 | Severino | A61B 5/044 600/523 |
| 2017/0055864 A1* | 3/2017 | Han | A61B 5/04011 |

OTHER PUBLICATIONS

Burkhard, W.A. et al., "Some Approaches to Best-Match File Searching", Communications of the ACM, Apr. 1973, pp. 230-236, vol. 16, No. 4.
Cardenes, Ruben et al., "Estimation of Electrical Pathways Finding Minimal Cost Paths from Electro-Anatomical Mapping of the Left Ventricle", Spanish Ministry of Scient and Innovation and eTorso project from Generalitat de Valenica, (2013-001404).
Cormen, Thomas H. et al., "Book Chapter Introduction to algorithms", Dijkstra's Algorithm (Book Chapter), MIT Press, 2001, pp. 595-601, Chapter 24.3.
Dijkstra, E.W., "A Note on Two Problems in Connexion with Graphs", Numerische Mathematik, (1959), pp. 269-271.
Horn, R.D. et al., "Proceedings of the Counterdrug Technology Assessment Center and Counterdrug Technology Assessment Center's ONDCP/CTAC International Symposium", Aug. 18-22, 1997, pp. 1201-1203. (Not Available from the J&J Copyright Clearance Center).
Koontz, Warren L.G. et al., "A Branch and Bound Clustering Algorithm" IEEE Transactions on Computers, Sep. 1975, pp. 908-915, vol. c-24, No. 9.
Sethian, J.A., "A fast marching level set method for monotonically advancing fronts", Proc. Natl. Acad. Sci. USA, Applied Mathematics, Feb. 1996, pp. 1591-1595, vol. 93.
European Search Report for European Patent Application No. 19158628.8, dated Jun. 3, 2019.

* cited by examiner

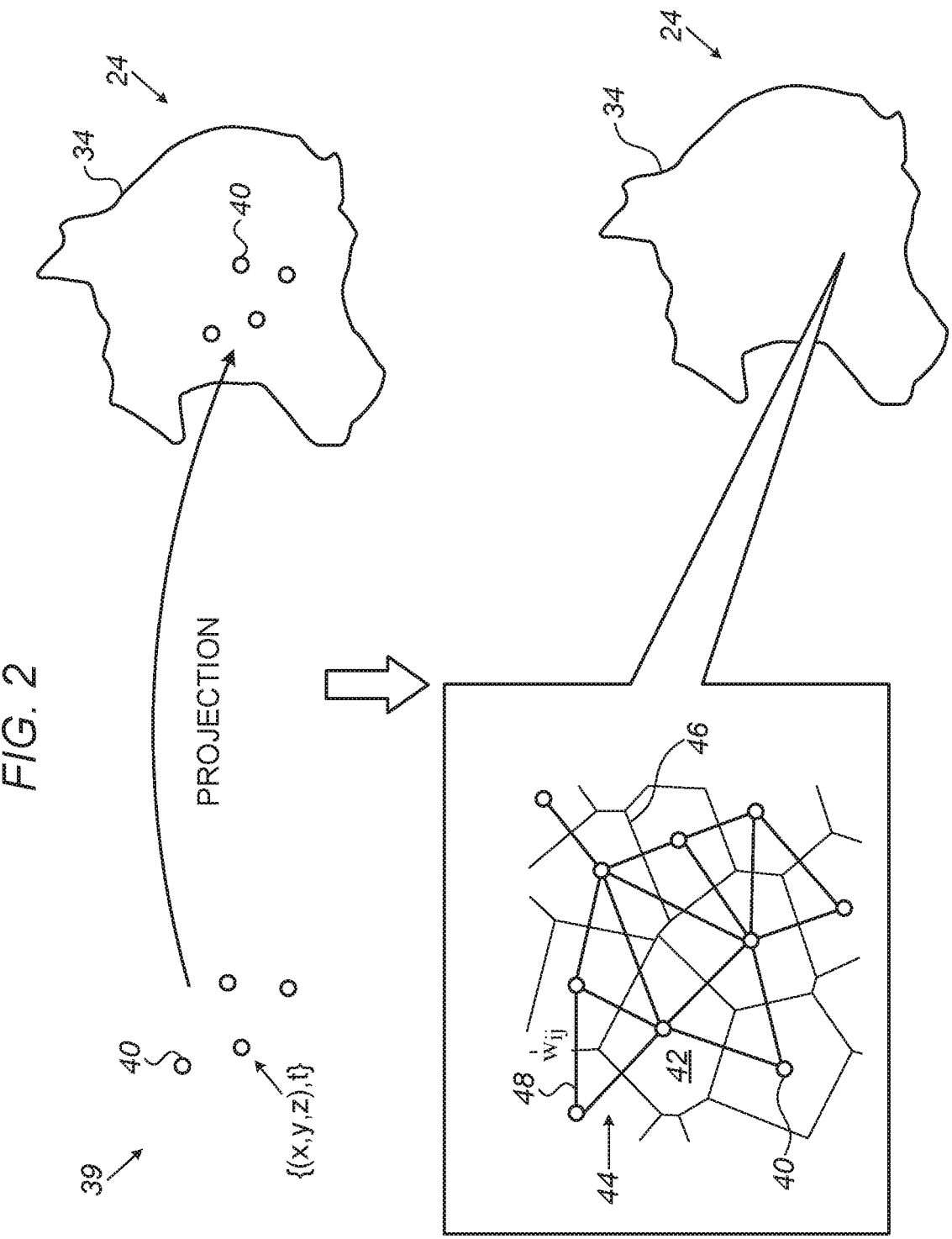

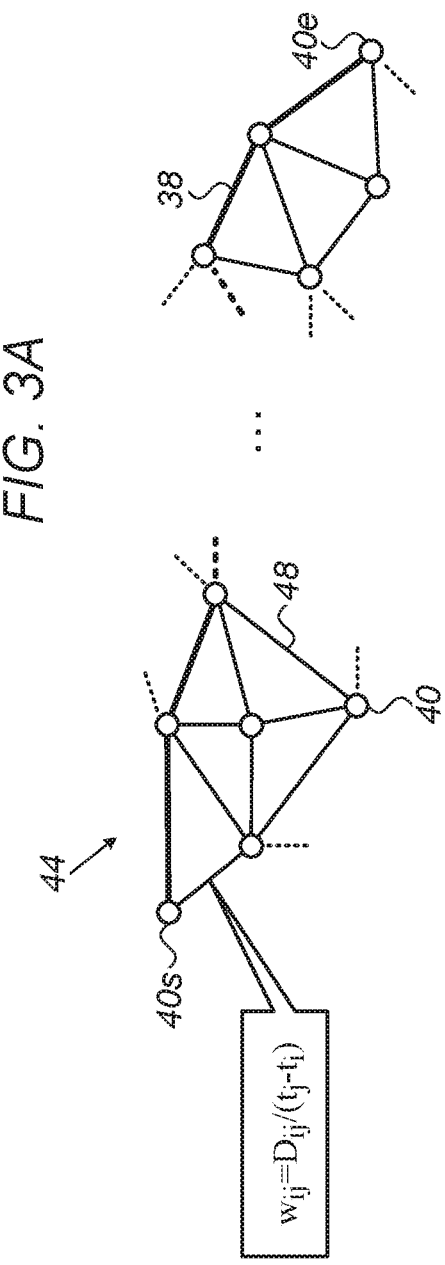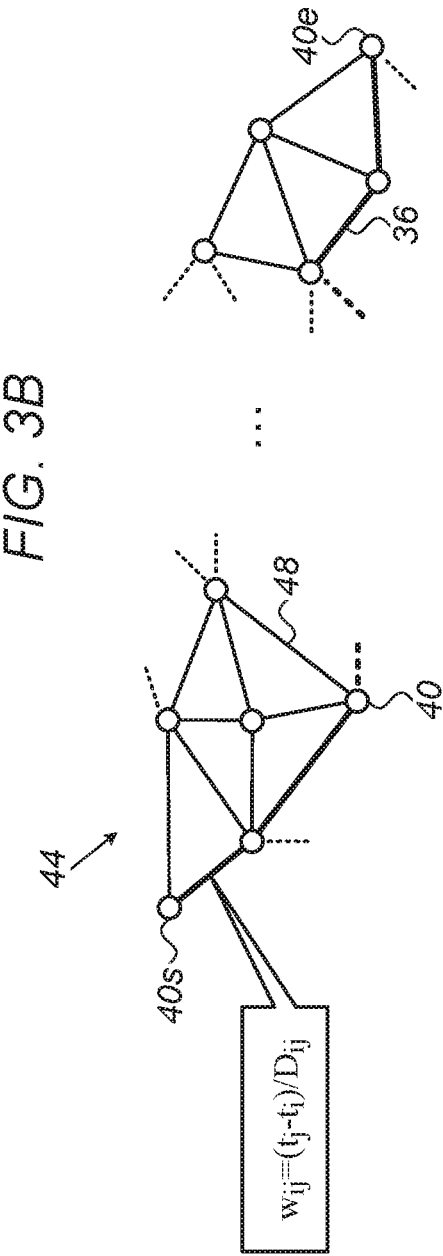

AUTOMATIC IDENTIFICATION OF MULTIPLE ACTIVATION PATHWAYS

FIELD OF THE INVENTION

The present invention relates to the field of electrophysiology, and particularly to the identification and treatment of cardiac arrhythmias.

BACKGROUND

A local activation time of a particular area of the heart is the time at which the wavefront of electrical propagation passes through the area. A local activation time is typically measured from a particular reference time, such as a particular point in time in the QRS complex of a body-surface electrocardiogram (ECG) recording.

Some types of cardiac arrhythmia are caused by the electrical activation of cardiac tissue over two or more separate activation pathways having different respective rates of propagation.

Cárdenes, Rubén, et al., "Estimation of electrical pathways finding minimal cost paths from electro-anatomical mapping of the left ventricle," International Workshop on Statistical Atlases and Computational Models of the Heart, Springer, Berlin, Heidelberg, 2013, presents a method to find electrical pathways using minimal cost paths computations on surface maps.

SUMMARY OF THE INVENTION

There is provided, in accordance with some embodiments of the present invention, an apparatus that includes a display and a processor. The processor is configured to construct a computerized electroanatomical model of a portion of a heart, the model including a mesh, which approximates the portion of the heart, and a plurality of points, at different respective locations on the mesh, having respective associated local activation times (LATs) that were ascertained from electrocardiographic signals acquired from the portion. The processor is further configured to identify, based on the respective locations of the points, a plurality of pairs of neighboring ones of the points, and to construct a graph that interconnects each of the identified pairs and is weighted by a plurality of first weights derived at least in part from the respective locations and LATs of the points, such that each interconnected pair has a respective first weight. The processor is further configured to identify a first pathway through the graph, from a first one of the points having a lowest one of the LATs to a second one of the points having a highest one of the LATs, that minimizes a first sum of the first weights over multiple pathways from the first point to the second point. The processor is further configured to reweight the graph by a plurality of second weights derived at least in part from the respective locations and LATs of the points, such that each interconnected pair has a respective second weight, identify a second pathway through the graph, from the first point to the second point, that minimizes a second sum of the second weights over the pathways, and display the mesh on the display, with the identified first pathway and second pathway superimposed over the mesh.

In some embodiments, for at least one interconnected pair, each of the first weight and the second weight is derived from (i) a distance between the interconnected pair, and (ii) a difference between the respective LATs of the interconnected pair.

In some embodiments, the distance is a geodesic distance with respect to a surface of the mesh.

In some embodiments, for the at least one interconnected pair, the first weight is a quotient of the distance and the difference, and the second weight is an inverse of the first weight.

In some embodiments, the processor is configured to identify the pairs of neighboring points by:
partitioning the mesh into a plurality of partitions, such that each one of the partitions contains a respective one of the points, and
identifying each pair of neighboring points in response to the pair being contained in any two of the partitions that border one another.

In some embodiments, the processor is configured to partition the mesh by computing a Voronoi tesselation of the mesh with respect to the points.

There is further provided, in accordance with some embodiments of the present invention, a method that includes constructing a computerized electroanatomical model of a portion of a heart, the model including a mesh, which approximates the portion of the heart, and a plurality of points, at different respective locations on the mesh, having respective associated local activation times (LATs) that were ascertained from electrocardiographic signals acquired from the portion. The method further includes, based on the respective locations of the points, identifying a plurality of pairs of neighboring ones of the points, and constructing a graph that interconnects each of the identified pairs and is weighted by a plurality of first weights derived at least in part from the respective locations and LATs of the points, such that each interconnected pair has a respective first weight. The method further includes identifying a first pathway through the graph, from a first one of the points having a lowest one of the LATs to a second one of the points having a highest one of the LATs, that minimizes a first sum of the first weights over multiple pathways from the first point to the second point. The method further includes reweighting the graph by a plurality of second weights derived at least in part from the respective locations and LATs of the points, such that each interconnected pair has a respective second weight, identifying a second pathway through the graph, from the first point to the second point, that minimizes a second sum of the second weights over the pathways, and displaying the mesh, with the identified first pathway and second pathway superimposed over the mesh.

There is further provided, in accordance with some embodiments of the present invention, a computer software product including a tangible non-transitory computer-readable medium in which program instructions are stored. The instructions, when read by a processor, cause the processor to construct a computerized electroanatomical model of a portion of a heart, the model including a mesh, which approximates the portion of the heart, and a plurality of points, at different respective locations on the mesh, having respective associated local activation times (LATs) that were ascertained from electrocardiographic signals acquired from the portion. The instructions further cause the processor to identify, based on the respective locations of the points, a plurality of pairs of neighboring ones of the points, and construct a graph that interconnects each of the identified pairs and is weighted by a plurality of first weights derived at least in part from the respective locations and LATs of the points, such that each interconnected pair has a respective first weight. The instructions further cause the processor to identify a first pathway through the graph, from a first one of the points having a lowest one of the LATs to a second one of the points having a highest one of the LATs, that minimizes a first sum of the first weights over multiple pathways from the first point to the second point. The instructions further cause the processor to reweight the graph by a plurality of second weights derived at least in part from the respective locations and LATs of the points, such that each interconnected pair has a respective second weight, identify a second pathway through the graph, from the first point to the second point, that minimizes a second sum of the second weights over the pathways, and display the mesh, with the identified first pathway and second pathway superimposed over the mesh.

There is further provided, in accordance with some embodiments of the present invention, a method that includes constructing a computerized electroanatomical model of a portion of a heart, the model including a mesh, which approximates the portion of the heart, and a plurality of points, at different respective locations on the mesh, having respective associated local activation times (LATs) that were ascertained from electrocardiographic signals acquired from the portion. The method further includes constructing a graph that interconnects the points. The method further includes, based on the respective locations and LATs of the points, identifying, from a plurality of pathways, through the graph, from a first one of the points having a lowest one of the LATs to a second one of the points having a highest one of the LATs, both a shortest pathway and a longest pathway, and displaying the mesh, with the identified shortest pathway and longest pathway superimposed over the mesh.

The present invention will be more fully understood from the following detailed description of embodiments thereof, taken together with the drawings, in which:

BRIEF DESCRIPTION OF THE DRAWINGS

FIG. 2 and FIGS. 3A-B collectively illustrate, schematically, a method for identifying activation pathways, in accordance with some embodiments of the present invention.

DETAILED DESCRIPTION OF EMBODIMENTS

Overview

Figure 1:
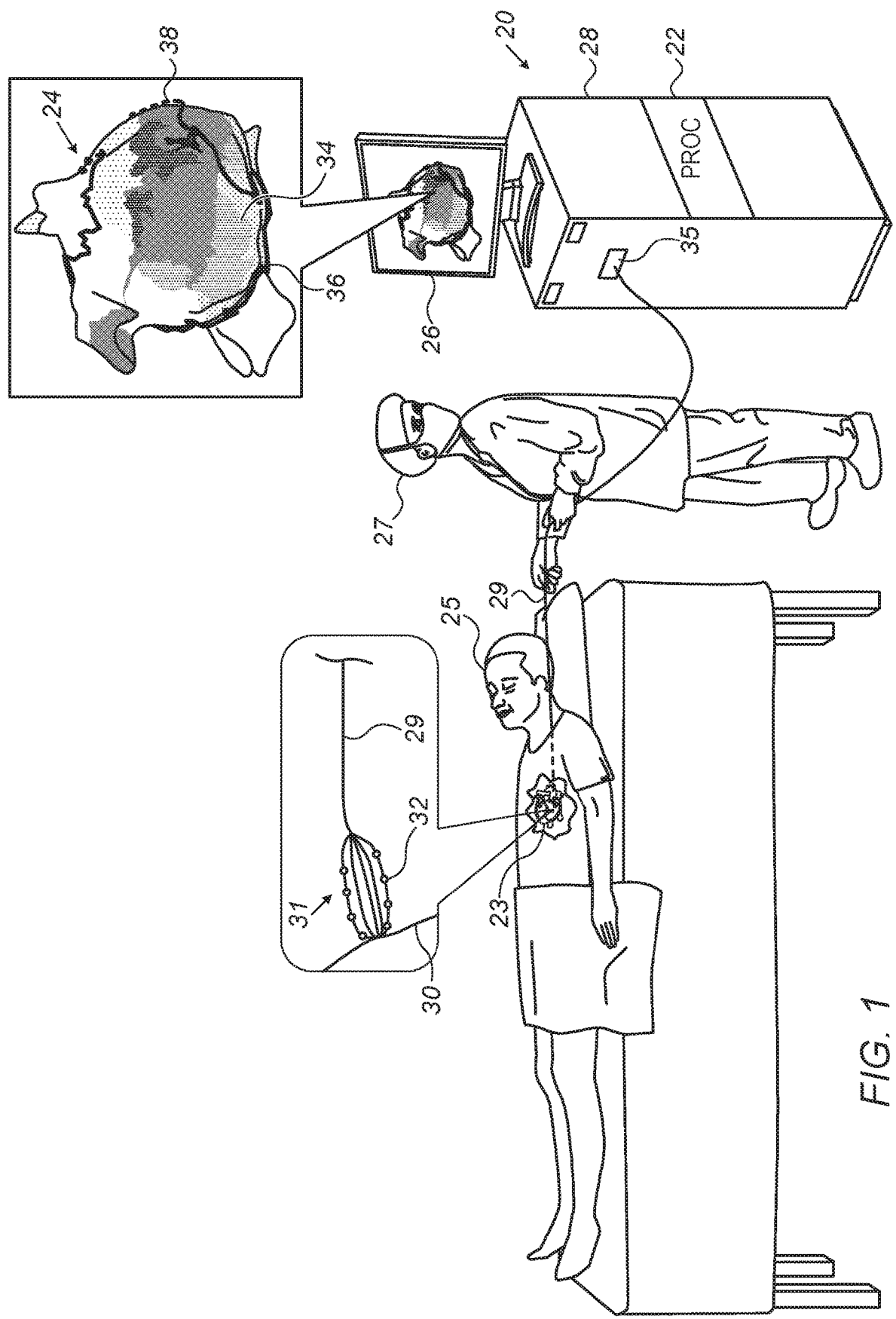
FIG. 1 is a schematic illustration of an electroanatomical mapping procedure, in accordance with some embodiments of the present invention.

In a cardiac electroanatomical mapping procedure, one or more electrodes, disposed at the distal end of a catheter, are used to acquire intracardiac electrocardiographic (ECG) signals from cardiac tissue, such as myocardial tissue, of a subject. From the acquired ECG signals, a processor may ascertain the local activation time (LAT) at various points on the tissue. The processor may then construct, and display, an electroanatomical map of the tissue, which includes an anatomical map of the relevant portion of the heart, annotated to indicate the ascertained LAT values. For example, the processor may project each point at which an LAT was acquired onto a mesh that models the relevant portion of the heart, and then color the mesh in accordance with the LATs.

Even when provided with such an electroanatomical map, however, it may be difficult for a physician to manually identify the activation pathway (or "propagation pathway") over which the electrical wavefront propagates across the tissue. It may be especially difficult for the physician to identify multiple activation pathways that propagate simultaneously.

To address this challenge, embodiments of the present invention provide techniques for automatically identifying one or more activation pathways on an electroanatomical map. For example, the processor may first identify the point having the lowest LAT value, referred to hereinbelow as the "start point," along with the point having the highest LAT value, referred to hereinbelow as the "end point." The processor may then compute both the fastest (i.e., longest) and slowest (i.e., shortest) propagation pathway from the start point to the end point. Subsequently, the processor may annotate the electroanatomical map to display both of the pathways.

In a healthy subject, the fastest and slowest pathways will be identical, or at least relatively close to one another. In a subject suffering from a cardiac arrhythmia, on the other hand, the two pathways may be relatively different. Hence, given the display of the two pathways, the physician may more readily diagnose, and treat, the subject. For example, the physician may decide to ablate some of the tissue over which the slowest pathway passes.

Typically, to compute the activation pathways, the processor first partitions the mesh surface into a plurality of regions, such that each region of the mesh surface contains a different respective one of the LAT points. For example, the processor may construct a Voronoi tesselation of the mesh surface, based on the points at which the LATs were acquired. The processor then identifies the neighboring LAT points of each given LAT point, by identifying those regions that border the region of the given LAT point. Subsequently, the processor constructs a graph that connects each of the LAT points to each of its neighbors, and then finds the slowest and fastest pathways that traverse the graph from the start point to the end point.

More particularly, to find the slowest activation pathway, the processor may weight each edge of the graph (with, possibly, a few exceptions, as further described below with reference to FIG. 3A) by the implied velocity between the two LAT points that are interconnected by the edge. This implied velocity may be defined, for example, as the quotient of the geodesic distance between the points and the difference between the respective LATs of the points. The processor may then find the path through the graph, from the start point to the end point, that minimizes the sum of the weights of the edges. Similarly, to find the fastest activation pathway, the processor may weight each edge (with, possibly, a few exceptions) by the inverse of the implied velocity, and then minimize the sum of the weights.

Advantageously, embodiments described herein do not, typically, interpolate the LAT points, or partition the mesh into a number of regions that is greater than the number of LAT points. As a result, the computation of the activation pathways is relatively fast.

System Description

Reference is initially made to FIG. 1, which is a schematic illustration of an electroanatomical mapping procedure, in accordance with some embodiments of the present invention.

FIG. 1 depicts a physician 27 performing an electroanatomical mapping procedure on a subject 25, using a catheter 29. The distal end 31 of catheter 29 comprises a plurality of electrodes 32. By navigating catheter 29 within the heart 23 of the subject, physician 27 causes electrodes 32 to contact, and acquire intracardiac ECG signals from, a portion of the heart (including, for example, a myocardial or epicardial surface of the heart), at a plurality of different locations. The ECG signals are received by a processor (PROC) 22.

Catheter 29 further comprises one or more position sensors (not shown), which continually output signals indicating the position and orientation of the catheter. Based on these signals, processor 22 ascertains the position of each of the electrodes, and hence, the anatomical location from which each ECG signal was acquired. Processor 22 further processes the ECG signals, such as to ascertain the LATs indicated by these signals. Using the ascertained LATs, along with a mesh 34 that approximates portion 30, the processor constructs a computerized electroanatomical model (or "map") 24 of portion 30.

In general, the processor may use any suitable technique to track the electrodes. For example, catheter 29 may comprise one or more electromagnetic position sensors, which, in the presence of an external magnetic field, generate signals that vary with the positions of the sensors. Based on these signals, the processor may ascertain the electrodes' respective locations. Alternatively, for each electrode, processor 22 may ascertain the respective impedances between the electrode and a plurality of external electrodes coupled to subject 25 at various different locations, and then compute the ratios between these impedances, these ratios being indicative of the electrode's location. As yet another alternative, the processor may use both electromagnetic tracking and impedance-based tracking, as described, for example, in U.S. Pat. No. 8,456,182, whose disclosure is incorporated herein by reference.

Subsequently to constructing model 24, processor 22 displays model 24 on a display 26. In displaying model 24, the processor annotates mesh 34 to indicate the ascertained LATs. For example, the processor may color mesh 34 in accordance with a color scale, such that varying LAT values are mapped to different respective colors, as indicated by the various hatch patterns in FIG. 1. The processor further superimposes, on mesh 34, both a fastest activation pathway 36 and a slowest activation pathway 38, which may be identified as described in detail below with reference to the subsequent figures.

(Typically, even when the LAT measurements are acquired from the myocardial surface of the heart, the surface of mesh 34 corresponds to the (convex) epicardial surface of the heart, rather than the (concave) myocardial surface, such that the information in model 24 may be more easily displayed.)

Typically, processor 22 resides within a console 28, which is coupled to catheter 29 via an electrical interface 35, such as a port or socket. The ECG signals from the electrodes, along with the position signals from the position sensors, are received, by processor 22, via electrical interface 35.

In general, processor 22 may be embodied as a single processor, or a cooperatively networked or clustered set of processors. Processor 22 is typically a programmed digital computing device configured to implement the functionality described herein in hardware, software, or any suitable combination of hardware and software elements. For example, at least some of the functionality of processor 22 may be implemented on an application-specific integrated circuit (ASIC), field-programmable gate array (FPGA), and/or graphics processing unit (GPU). Alternatively or additionally, the processor may comprise a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Reference is now made to FIG. 2 and to FIGS. 3A-B, which collectively illustrate, schematically, a method for identifying activation pathways, in accordance with some embodiments of the present invention.

The top portion of FIG. 2 shows the construction of model 24. Typically, to construct model 24, the processor first builds mesh 34, based on an anatomical mapping procedure performed in advance of the procedure described above with reference to FIG. 1. Typically, mesh 34 is a triangular mesh, comprising a plurality of connected triangles that collectively approximate (or "model") the relevant portion of the heart.

The processor also acquires a point cloud 39 of LAT points 40, by processing any intracardiac ECG signals received from electrodes 32, as described above with reference to FIG. 1. Each such point 40 has an associated three-dimensional coordinate "(x,y,z)" that describes the location of the point, and an associated LAT "t," which is the LAT acquired at coordinate (x,y,z). (Although, for ease of illustration, the top portion of FIG. 2 shows only a few points 40, it is noted that, in practice, point cloud 39 typically includes at least several hundred points.) Subsequently to acquiring point cloud 39, the processor projects point cloud 39 onto mesh 34, such that each point 40 is mapped to the appropriate location on mesh 34. The processor also identifies the point 40 having the smallest LAT, referred to hereinbelow as the "start point," along with the point 40 having the largest LAT, referred to hereinbelow as the "end point."

In other embodiments, the anatomical mapping of the relevant portion of the subject's heart is performed concurrently with the acquisition of points 40, such that points 40 are already defined in the coordinate system of mesh 34, and a projection of points 40 may, therefore, not be necessary.

Subsequently to constructing model 24, the processor identifies, based on the LATs and on the respective locations of points 40 on the mesh, both a slowest activation pathway and a fastest activation pathway. The slowest activation pathway passes from the start point to the end point with a minimum velocity, relative to the other activation pathways that pass from the start point to the end point; hence, the slowest activation pathway is also the shortest activation pathway. Conversely, the fastest activation pathway passes from the start point to the end point with a maximum velocity, relative to the other activation pathways; hence, the fastest activation pathway is also the longest activation pathway.

Typically, to identify each of the slowest and fastest activation pathways, the processor first constructs a weighted graph 44, in which points 40 are interconnected by a plurality of edges 48 having respective weights that are derived, at least in part, from the respective locations and LATs of the points. (In other words, at least some of the weights are derived from the respective locations and LATs of at least some of the points.) The processor then optimizes a function of the weights over all of the legitimate pathways, through the graph, that connect the start point to the end point. (A legitimate pathway is any pathway along which the LAT is strictly increasing.)

To construct graph 44, the processor first identifies each pair of neighboring LAT points. Subsequently, for each of the identified pairs of neighboring points ($40_i$, $40_j$) having respective LATs ($t_i$, $t_j$), where $t_j > t_i$, the processor computes a weight $w_{ij}$. The processor then constructs graph 44, such that graph 44 interconnects each of the identified pairs with the weight that was computed for the pair. In other words, the processor constructs graph 44 such that each edge 48 connecting any given pair of neighboring points has the weight that was computed for the pair.

Typically, for most or all of the interconnected pairs of points, the weight for the pair is derived from the distance $D_{ij}$ between the pair and the difference $t_j - t_i$ between the respective LATs of the pair. For example, to identify the slowest activation pathway, as further described below with reference to FIG. 3A, the processor may calculate the weight between $40i$ and $40j$ as $D_{ij}/(t_j - t_i)$, i.e., the velocity between the points that is implied by the respective locations and LATs of the points. Conversely, to identify the fastest activation pathway, as further described below with reference to FIG. 3B, the processor may calculate the weight as $(t_j - t_i)/D_{ij}$, i.e., the inverse of the implied velocity.

Typically, the distance $D_{ij}$ between the pair of neighboring points, which is used for calculating $w_{ij}$, is the geodesic distance, with respect to the surface of mesh 34, between the pair of points. To calculate the geodesic distances between the points, the processor may use any suitable method, such as the fast marching method, which is described in Sethian, James A., "A fast marching level set method for monotonically advancing fronts," Proceedings of the National Academy of Sciences 93.4 (1996): 1591-1595, which is incorporated herein by reference.

Typically, to identify each pair of neighboring points, the processor partitions mesh 34 into a plurality of partitions 42, such that each of partitions 42 contains a different respective one of LAT points 40. (Partitions 42 may alternatively be referred to as "cells" or "regions.") For example, the processor may compute a Voronoi tesselation of the mesh with respect to the LAT points, such that every point within any given partition 42 is closer to the LAT point that is contained within the partition than to any other LAT point. Subsequently, the processor identifies each pair of neighboring LAT points in response to the pair being contained in any two of the partitions that border one another along a common border 46. In other words, the processor identifies each pair of partitions that border one another, and then identifies, as neighbors, the LAT points that are contained, respectively, within these two partitions.

FIG. 3A shows the identification of slowest activation pathway 38 between a start point 40s and an end point 40e, using graph 44. (The identified pathway is indicated by the thickened edges of graph 44.) Typically, to identify the slowest activation pathway, the processor computes the weight $w_{ij}$ for most, or all, pairs of neighboring points ($40_i$, $40_j$) as the implied velocity between the two points, i.e., the quotient of $D_{ij}$ and $t_j - t_i$. Subsequently, the processor minimizes the sum of the computed weights over multiple pathways that connect start point 40s to end point 40e. In other words, the processor finds the connected sequence of edges 48 that connects start point 40s to end point 40e and has a minimum sum of weights, relative to other connected sequences of edges connecting start point 40s to end point 40e. To minimize the sum of the weights, the processor may use any suitable algorithm, such as Dijksta's algorithm or the fast marching method.

In some cases, the processor may enforce a predetermined minimum velocity $v_{min}$, i.e., the processor may compute the weights by applying the function $w_{ij} = \max(D_{ij}/(t_j - t_i), v_{min})$. Thus, for example, most of the weights may be computed as $D_{ij}/(t_j - t_i)$, while the rest of the weights may be computed as $v_{min}$. Alternatively or additionally, the processor may set the respective weights for one or more edges to infinity, to prevent any pathway from passing over these edges, in response to these edges passing through non-conductive tissue.

FIG. 3B shows the identification of the fastest activation pathway 36 between start point 40s and end point 40e. Typically, to identify the fastest activation pathway, the processor computes the weight for most, or all, pairs of neighboring points as the inverse of the implied velocity between the points. As described above for the identification of the slowest activation pathway, the processor may enforce a maximum inverse velocity, and/or set one or more weights to infinity. Subsequently, the processor minimizes the sum of the computed weights over multiple pathways that connect start point 40s to end point 40e, using Dijksta's algorithm, the fast marching method, or any other suitable algorithm. (It is noted that a single execution of fast marching may be used for both computing the geodesic distances between the points, and finding the fastest or slowest activation pathway.)

Advantageously, subsequently to identifying one of the activation pathways, the processor does not need to reconstruct graph 44 to identify the other activation pathway. Rather, the processor may simply compute the necessary weights, reweight the graph by the new weights, and then minimize the sum of the new weights as described above.

In some embodiments, as described above, each edge in graph 44 has a single weight, which quantifies the velocity, or inverse thereof, in moving from the lower-LAT point to the higher-LAT point. In such embodiments, the weight-sum-minimizing algorithm considers only legitimate pathways, along which the LAT is strictly increasing. Alternatively, illegitimate pathways may be avoided by assigning two weights to each edge: a first weight $w_{ij}$, which, as described above, is associated with moving from the lower-LAT point $40_i$ to the higher-LAT point $40_j$, and a second weight $w_{ji}$, which is infinite. Using this scheme, any pathway that proceeds from $40_j$ to $40_i$ will perforce not be selected by the weight-sum-minimizing algorithm, due to having an infinite sum of weights.

As described above with reference to FIG. 1, subsequently to identifying the fastest and slowest activation pathways, the processor displays the mesh that approximates the relevant cardiac anatomy, with the identified pathways superimposed over the mesh. Alternatively or additionally to identifying and displaying the fastest and slowest activation pathways, the processor may identify and display any other suitable activation pathway, by choosing appropriate weights for graph 44.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
   one or more processors; and
   a non-transitory computer readable medium storing a plurality of instructions, which when executed, cause the one or more processors to:
   construct a computerized electroanatomical model of a portion of a heart, the model including a mesh, which approximates the portion of the heart, and a plurality of points, at different respective locations on the mesh, having respective associated local activation times (LATs) that were ascertained from electrocardiographic signals acquired from the portion,
   based on the respective locations of the points, identify a plurality of pairs of neighboring ones of the points,
   construct a graph that interconnects each of the identified pairs and is weighted by a plurality of first weights derived at least in part from the respective locations and LATs of the points, such that each interconnected pair has a respective first weight,
   identify a first pathway through the graph, from a first one of the points having a lowest one of the LATs to a second one of the points having a highest one of the LATs, that minimizes a first sum of the first weights over multiple pathways from the first point to the second point, the identified first pathway being designated as a slowest activation pathway,
   reweight the graph by a plurality of second weights derived at least in part from the respective locations and LATs of the points, such that each interconnected pair has a respective second weight,
   derive, for at least one interconnected pair, each of the first weight and the second weight from a distance between the interconnected pair and a difference between the respective LATs of the interconnected pair,
   identify a second pathway through the graph, from the first point to the second point, that minimizes a second sum of the second weights over the pathways, the identified second pathway being designated as a fastest activation pathway, and
   display the mesh on the display, with the identified first pathway and second pathway superimposed over the mesh.

2. The apparatus according to claim 1, wherein the distance is a geodesic distance with respect to a surface of the mesh.

3. The apparatus according to claim 1, wherein, for the at least one interconnected pair, the first weight is a quotient of the distance and the difference, and the second weight is an inverse of the first weight.

4. The apparatus according to claim 1, wherein the processor is configured to identify the pairs of neighboring points by:
   partitioning the mesh into a plurality of partitions, such that each one of the partitions contains a respective one of the points, and
   identifying each pair of neighboring points in response to the pair being contained in any two of the partitions that border one another.

5. The apparatus according to claim 4, wherein the processor is configured to partition the mesh by computing a Voronoi tesselation of the mesh with respect to the points.

6. A method, comprising:
   constructing a computerized electroanatomical model of a portion of a heart, the model including a mesh, which approximates the portion of the heart, and a plurality of points, at different respective locations on the mesh, having respective associated local activation times (LATs) that were ascertained from electrocardiographic signals acquired from the portion;
   based on the respective locations of the points, identifying a plurality of pairs of neighboring ones of the points;
   constructing a graph that interconnects each of the identified pairs and is weighted by a plurality of first weights derived at least in part from the respective locations and LATs of the points, such that each interconnected pair has a respective first weight;
   identifying a first pathway through the graph, from a first one of the points having a lowest one of the LATs to a second one of the points having a highest one of the LATs, that minimizes a first sum of the first weights over multiple pathways from the first point to the second point, the identified first pathway being designated as a slowest activation pathway;
   reweighting the graph by a plurality of second weights derived at least in part from the respective locations and LATs of the points, such that each interconnected pair has a respective second weight;
   deriving, for at least one interconnected pair, each of the first weight and the second weight from a distance between the interconnected pair and a difference between the respective LATs of the interconnected pair;
   identifying a second pathway through the graph, from the first point to the second point, that minimizes a second sum of the second weights over the pathways, the identified second pathway being designated as a fastest activation pathway; and
   displaying the mesh, with the identified first pathway and second pathway superimposed over the mesh.

7. The method according to claim 6, wherein the distance is a geodesic distance with respect to a surface of the mesh.

8. The method according to claim 6, wherein, for the at least one interconnected pair, the first weight is a quotient of the distance and the difference, and the second weight is an inverse of the first weight.

9. The method according to claim 6, wherein identifying the pairs of neighboring points comprises:
   partitioning the mesh into a plurality of partitions, such that each one of the partitions contains a respective one of the points; and
   identifying each pair of neighboring points in response to the pair being contained in any two of the partitions that border one another.

10. The method according to claim 9, wherein partitioning the mesh comprises partitioning the mesh by computing a Voronoi tesselation of the mesh with respect to the points.

11. A computer software product comprising a tangible non-transitory computer-readable medium in which program instructions are stored, which instructions, when read by a processor, cause the processor to:
    construct a computerized electroanatomical model of a portion of a heart, the model including a mesh, which approximates the portion of the heart, and a plurality of points, at different respective locations on the mesh, having respective associated local activation times (LATs) that were ascertained from electrocardiographic signals acquired from the portion, based on the respective locations of the points, identify a plurality of pairs of neighboring ones of the points, construct a graph that interconnects each of the identified pairs and is weighted by a plurality of first weights derived at least in part from the respective locations and LATs of the points, such that each interconnected pair has a respective first weight, identify a first pathway through the graph, from a first one of the points having a lowest one of the LATs to a second one of the points having a highest one of the LATs, that minimizes a first sum of the first weights over multiple pathways from the first point to the second point, the identified first pathway being designated as a slowest activation pathway, reweight the graph by a plurality of second weights derived at least in part from the respective locations and LATs of the points, such that each interconnected pair has a respective second weight, derive, for at least one interconnected pair, each of the first weight and the second weight from a distance between the interconnected pair and a difference between the respective LATs of the interconnected pair, identify a second pathway through the graph, from the first point to the second point, that minimizes a second sum of the second weights over the pathways, the identified second pathway being designated as a fastest activation pathway, and display the mesh, with the identified first pathway and second pathway superimposed over the mesh.

12. The computer software product according to claim 11, wherein the distance is a geodesic distance with respect to a surface of the mesh.

13. The computer software product according to claim 11, wherein, for the at least one interconnected pair, the first weight is a quotient of the distance and the difference, and the second weight is an inverse of the first weight.

14. The computer software product according to claim 11, wherein the instructions cause the processor to identify the pairs of neighboring points by:

partitioning the mesh into a plurality of partitions, such that each one of the partitions contains a respective one of the points, and identifying each pair of neighboring points in response to the pair being contained in any two of the partitions that border one another.

15. The computer software product according to claim 14, wherein the instructions cause the processor to partition the mesh by computing a Voronoi tesselation of the mesh with respect to the points.

* * * * *